United States Patent
Morgan et al.

(10) Patent No.: US 12,029,719 B2
(45) Date of Patent: Jul. 9, 2024

(54) COMPOUNDS COMPRISING CANNABINOIDS AND OTHER NATURAL INGREDIENTS FOR ALIEVING PREMENSTRUAL, MENSTRUAL AND MENOPAUSAL SYMPTOMS

(71) Applicants: Allen Morgan, West Allenhurst, NJ (US); Ariel Maxine Morgan, West Allenhurst, NJ (US); Karen Elizabeth Morgan, West Allenhurst, NJ (US)

(72) Inventors: Allen Morgan, West Allenhurst, NJ (US); Ariel Maxine Morgan, West Allenhurst, NJ (US); Karen Elizabeth Morgan, West Allenhurst, NJ (US)

( * ) Notice: Subject to any disclaimer, the term of this patent is extended or adjusted under 35 U.S.C. 154(b) by 0 days.

(21) Appl. No.: 17/722,918

(22) Filed: Apr. 18, 2022

(65) Prior Publication Data

US 2022/0331287 A1    Oct. 20, 2022

Related U.S. Application Data

(60) Provisional application No. 63/176,008, filed on Apr. 16, 2021.

(51) Int. Cl.
  *A61K 31/352* (2006.01)
  *A61K 36/185* (2006.01)
  *A61P 5/24* (2006.01)

(52) U.S. Cl.
  CPC .......... *A61K 31/352* (2013.01); *A61K 36/185* (2013.01); *A61P 5/24* (2018.01)

(58) Field of Classification Search
  None
  See application file for complete search history.

(56) References Cited

U.S. PATENT DOCUMENTS

| | | | |
|---|---|---|---|
| 4,876,276 A | 10/1989 | Mechoulam et al. | |
| 5,227,537 A | 7/1993 | Stoss et al. | |
| 5,846,566 A | 12/1998 | Burguiere et al. | |
| 6,022,562 A | 2/2000 | Autant et al. | |

FOREIGN PATENT DOCUMENTS

| | | | | |
|---|---|---|---|---|
| CA | 3068383 | * | 1/2019 | |
| CA | 3068383 A1 | * | 1/2019 | ............. A61K 31/01 |

OTHER PUBLICATIONS

Agurell et al., "Pharmacokinetics and metabolism of ?1-tetrahydrocannabinol and other cannabinoids with emphasis on man," Pharmacol. Rev., 1986; 38(1): pp. 21-43.

Consroe et al., "Antiepileptic Potential of Cannabidiol Analogs," J. Clin. Pharmacol., 1981; 21(S1): pp. 428S-436S.

* cited by examiner

*Primary Examiner* — Michael V Meller
(74) *Attorney, Agent, or Firm* — Arnall Golden Gregory LLP

(57) ABSTRACT

The present application discloses natural compositions as medicaments and wellness products comprising of one or more cannabinoids and little or no THC comprised with other natural ingredients used for alleviating premenstrual, menstrual, and menopausal symptoms such as hot flashes, night sweats, mood changes, nausea, and Premenstrual Syndrome (PMS). The invention also contemplates methods of use of said compositions.

1 Claim, No Drawings

COMPOUNDS COMPRISING CANNABINOIDS AND OTHER NATURAL INGREDIENTS FOR ALIEVING PREMENSTRUAL, MENSTRUAL AND MENOPAUSAL SYMPTOMS

CROSS-REFERENCE TO RELATED APPLICATIONS

This application claims the benefit of U.S. Provisional Application 63/176,008 filed Apr. 16, 2021, the entire contents of which are hereby incorporated by reference in its entirety.

BACKGROUND OF THE INVENTION

The physical and emotional symptoms of premenstrual, menstrual, and menopausal states may result from the fluctuation of hormones accompanying the female menstrual cycle. Symptoms associated with premenstrual syndrome, menstruation, and menopause are varied and range from mild to incapacitating, are a major cause of discomfort to women causing substantial discomfort as well as loss of time and money. These symptoms include, but are not limited to dysmenorrhea (menstrual cramping), irritability, water retention, moodiness, depression, cramping, anxiety, skin changes, headaches, breast tenderness or pain, tension, weight gain, cravings, fatigue, increased stress, and hot flashes and mood swings. Symptoms of conditions can include itching and other associated sensory maladies. Many of these symptoms are due to changes in hormonal levels throughout the menstrual cycle. Menstrual cramping is associated with increased levels of prostaglandin 2a, prostaglandin E2, and in some cases leukotrienes in the endometrium and menstrual fluid. These eicosinoids lead to restricted blood flow to the uterus and increased uterine contractions, causing pain. One example is dysmenorrhea, which is the occurrence of painful uterine cramps during menstruation that affects a large number of post-pubescent women. The pain of dysmenorrhea originates in the uterus or from ectopic endometrial tissue in the case of endometriosis.

The botanical may be, but is not limited to, turmeric, ginger, fennel, valerian root, and cramp bark *Agnus castus*, aloe vera, comfrey, calendula, dong quai, black cohosh, chamomile, evening primrose, *Hypericum perforatum*, licorice root, black currant seed oil, St. John's wort, tea extracts, lemon balm, *capsicum*, rosemary, *Areca catechu*, mung bean, borage seed oil, witch hazel, fenugreek, lavender, soy, heath, cranberries, blueberries, azaleas, red onion skin, short red bell peppers, long red bell peppers, beet root extract, capsanthin, whortleberry, lingenberry, chokeberry, sweet rowan, rowanberry, seabuckhrouberry, crowberry, strawberries, or gooseberries.

Cannabinoids are a class of diverse chemical compounds that act on cannabinoid receptors in cells and potentially alter neurotransmitter release in the brain. Many cannabinoids have been identified from *cannabis*, of which the two most prominent and intensively studied are cannabidiol (CBD) and tetrahydrocannabinol (THC).

CBD, a cannabinoid constituent of *cannabis* plants, possesses anxiolytic, antipsychotic, antiemetic and anti-inflammatory properties, without exhibiting the psychoactive effects of THC. THC and CBD are synthesized in the plant as DELTA 9-tetrahydrocannabinolic acid and cannabidiolic acid from the common precursor olivetol.

Both THC and CBD exert their effects by interacting with the G protein-coupled cannabinoid receptors (GPCRs), CB1 and CB2 with varying affinities. CB1 receptors are expressed in larger quantities in the brain and regions in the central nervous system, and in lower amounts in peripheral tissues; the CB2 receptors have been identified to be localized to immune cells, tonsils and the spleen. The CB1 receptors appear to play significant roles in pain perception, memory, motor regulation, appetite, mood and sleep, whereas the CB2 receptors are linked with anti-inflammation, pain reduction and reducing tissue damage. Upon activation by endocannabinoids like anandamide and 2-arachidonylglycerol (2-AG) (which are short lived), CB1 and CB2 trigger downstream cascades that help mediate homeostasis and healthy functioning. In contrast, the plant-derived cannabinoids THC and CBD that directly or indirectly interact with CB1 and CB2 with varying affinities modulate the activities of these receptors for prolonged durations.

Great interest is also apparent for cannabigerol (CBG), and cannabinol (CBN). The *cannabis* plant, also known as hemp or marijuana, has been used throughout agricultural history as a source of an intoxicant, medicine and fiber. The medical use of *cannabis* is deeply rooted in history. For almost 5,000 years, *cannabis* and preparations produced from it have been used for applications including treating nausea, inflammation, vomiting and pain. The most studied component of the *cannabis* plant is a group of chemicals called cannabinoids or phytocannabinoids. Cannabinoids largely contribute to the *cannabis* plant's medical and recreational properties.

THC is the major psychoactive cannabinoid found in *cannabis* and mimics the action of the endogenous cannabinoid receptor ligands anandamide and 2-AG by activating both CB1 and CB2 receptors. Due to its binding to CB1 receptors which are specifically present in the central nervous system in areas associated with pain (e.g., spinal trigeminal nucleus, amygdala, basal ganglia and periaqueductal gray), THC possesses antinociceptive activity and is hence used as an analgesic agent in certain pain medications. In addition, THC has also been shown to be effective in the treatment of glaucoma, nausea, chronic pain, multiple sclerosis, epilepsy and inflammation in several pre-clinical and clinical studies. Unfortunately, THC abuse is common and stymies complete legalization of the chemical due to the accompanying behavioral and psychological dependence; DELTA 9-THC has remained a subject of controversy.

CBD, which is the non-psychoactive plant-derived cannabinoid, and a promising therapeutic agent, has gained increasing attention because it has many of the beneficial qualities of THC without the behavioral and psychological dependence. Accordingly, CBD is a recognized potential therapeutic agent for various disorders of the central nervous system including anxiety, epilepsy, schizophrenia, Parkinson's disease, Alzheimer's disease, multiple sclerosis and many more. Unlike THC, CBD does not appear to activate CB1 and CB2, and instead blocks, by complex mechanisms, the ligands that activate these receptors. Several groups have proposed that this activity not only results in the non-psychotropic effects exhibited by CBD but may also account for ameliorating some of the psychotropic effects shown by THC. In addition, by lowering the psychoactivity of THC, CBD may also potentiate some of THC's benefits by enhancing its tolerability and widening its therapeutic window. Thus, use of CBD along with THC can have distinct advantages.

CBD can also inhibit or delay the re-uptake and hydrolysis of endocannabinoids like anandamide and adenosine. CBD has also been hypothesized to interact with several other non-endocannabinoid signaling systems such as serotonin receptors, vanilloid receptors, GPR-55 (orphan receptors), and peroxisome proliferator activated receptors (PPARs), making it a possible "multi-target drug". In addition to these activities, the polyphenolic ring in CBD also results in it being a potent antioxidant. All these properties have prompted the exploration of the therapeutic potential of CBD for a range of neuropsychiatric as well as inflammatory disorders; unfortunately in its most common oil form it can present formulation problems.

The oral route is the most commonly acceptable delivery mechanism for drug and nutraceuticals. However, sublingual and topical delivery is also useful, but can have limited uptake potential. Lipid solubility and molecular size are the major limiting factors for molecules to pass through biological membranes and to be absorbed systemically following oral or topical administration. High lipophilicity of cannabinoids results in poor dissolution in the aqueous environment of the gastrointestinal tract. It not only makes this class of compounds poorly absorbed systemically from oral dosage forms, but complicates the physiologic effects. The low bioavailability of oral cannabinoids thereby restricts their therapeutic and supplement uses.

Currently, there are only a few approved oral formulations of cannabinoids commercially available for treating nausea, vomiting associated with cancer, multiple sclerosis, intractable cancer pain, etc. There is a need for novel and effective oral formulations of cannabinoids that can be applied not only to pharmaceutical, but also food, beverage and supplement applications as well as topical use.

SUMMARY OF THE INVENTION

We have found that inclusion of CBD with a number of different natural ingredients provides an unexpectedly superior formulation for the alleviation of pain and symptoms associated with the menstrual cycle or with the changes that occur during menopause. The use of the combination of ingredients appears to benefit the patient more than simply an additive effect, suggesting these chemicals act to provide a synergistic effect. While topical forms of the invention are useful and contemplated, it is believed that ingestion of the composition provides the easiest route of administration. The medicament can be orally administered for immediate release or compounded in a timed release form so that it can be taken less often to assist in patient compliance.

Definitions

Unless specifically noted otherwise herein, the definitions of the terms used are standard definitions used in the art of organic synthesis and pharmaceutical sciences. It is intended that the embodiments, aspects and variations are to be considered illustrative and not limiting.

"PMS" or "premenstrual syndrome" refers to physical and emotional symptoms experienced by women during the luteal phase of their menstrual cycle, typically in the days immediately before the onset of menstruation.

"Physical symptoms" refers to physical symptoms of PMS including but not limited to PMS-related pain (such as backache, headache, generalized aches and pains), breast tenderness, bloating, and cramping (such as in the abdomen).

"Emotional symptoms" refers to emotional symptoms of PMS including but not limited to irritability and mood swings/changes.

The phrase "alleviating menstrual and menopausal" means that a reduction in severity of PMS symptoms.

The phrase "menstrual and menopausal symptoms" includes but is not limited to perimenopause, menopause/post-menopause.

"Menopause" or "menopausal" refers to the period that marks the permanent cessation of menstrual activity.

"Post-menopause" refers to the period after the cessation of menstrual activity.

"Stress" refers to the negative "wear and tear" the body experiences as a person adjusts to changes in their environment that occur on a regular, daily basis.

The term "cannabinoid" is defined as one of a class of diverse compounds that acts on cannabinoid receptors in cells that alter neurotransmitter release in the brain. Cannabinoid may comprise all ligands of the cannabinoid receptor and related compounds, including the endocannabinoids (produced naturally in the body by animals), the phytocannabinoids (found in *cannabis* and some other plants), and synthetic cannabinoids that may be manufactured artificially.

In one aspect, the term "cannabidiol" or "CBD" is a phytocannabinoid that is one of more than 113 active cannabinoids that have been identified in *cannabis*. CBD may account for up to 40% of the plant's extract, and has been considered to provide a large scope of potential medicinal applications. In another aspect, the term "cannabinoid" is a compound (such as cannabinol, THC, cannabigerol, or cannabinol) that is found in the plant species *Cannabis saliva* (known as both hemp and marijuana), and includes metabolites and synthetic analogues thereof, that may or may not have psychoactive properties. Cannabinoids include compounds, such as THC, that have high affinity for the cannabinoid receptor, and compounds that do not have significant affinity for the cannabinoid receptor, such as cannabidiol (CBD). Cannabinoids also include compounds that have a characteristic dibenzopyran ring structure (such as in THC) and cannabinoids which do not have a pyran ring (such as cannabidiol). Cannabinoids also include, for example, THC, CBD, dimethyl heptylpentyl cannabidiol (DMHP-CBD) and 6,12-dihydro-6-hydroxy-cannabidiol (see U.S. Pat. Nos. 5,227,537 and 4,876,276, which are herein incorporated by reference in their entirety); and cannabidiol (−)(CBD) analogs. See Consroe et al., J. Clin. Pharmacol. 21:428S-436S, 1981 and Agurell et al., Pharmacol. Rev. 38:31-43, 1986, which are all incorporated herein by reference in its entirety. Accordingly, the term "*cannabis* oil" may comprise of these cannabinoids, including CBD, THC, 11-OH-THC and 11-NOR-9-Carboxy-THC, and other compounds as disclosed herein.

The term THC can include a number of compounds. The most potent stereoisomer occurs naturally as THC where the two chiral centers at C-6a and C-10a are in the trans-configuration as the (−)-trans-isomer, and this stereoisomer is also known as dronobinol. There are seven double bond isomers in the partially saturated carboxylic ring. Tetrahydrocannabinol, such as Delta-THC, helps reduce nausea and vomiting, which is particularly beneficial to patients undergoing chemotherapy for cancer. Patients suffering from AIDS often experience a lack of appetite, of which THC is also helpful in counteracting. THC is also useful for glaucoma relief.

As used herein, the term "CBD and THC" or "CBD/THC" includes substantially pure CBD, substantially pure THC or a mixture of CBD and THC having the particular purity, CBD/THC ratio and concentrations as disclosed in the present application. For example, a composition comprising "CBD and THC" includes at least one of 1) substantially pure CBD without THC, 2) substantially pure THC without CBD, and 3) a mixture of both CBD and THC having the purity, concentrations and ratios as disclosed herein.

The term "neutraceutical" or "nutraceutical" is a combination of the terms "nutritional" and "pharmaceutical". It refers to a composition that is known or suspected to positively affect human nutrition and/or health.

The term "THC" or its main isomer (−)-trans-Delta 9-tetrahydrocannabinol, is the principal psychoactive constituent (or a cannabinoid) of *cannabis*. THC has been employed effectively for the treatment of anorexia in patients with HIV/AIDS and for refractory nausea and vomiting in patients undergoing chemotherapy. THC is an aromatic terpenoid that has very low solubility in water.

CBD can occur in up to 40% of simple cannabinoid extracts from *cannabis*. CBD generally occurs in the *cannabis* plant prior to processing as CBDA which has a carboxylic acid group. The 2-carboxylic acids of the cannabinoids, including CBD, can be decarboxylated by heat, light, or alkaline conditions to their respective decarboxylated compounds.

Cannabinoids have been shown effective in treating inflammation, diabetes, cancer, mood disorders (PTSD to ADD) and neurodegenerative disease such as Alzheimer's. It has been shown to have anti-convulsive, anti-anxiety, anti-psychotic, anti-nausea and anti-rheumatoid arthritic and sedative properties, and a clinical trial showed that it eliminates anxiety and other unpleasant psychological side effects. CBD does not display the psychoactive effects of THC. CBD was found in one study to be more effective than aspirin for pain relief and reducing inflammation. CBD has been shown to be a potent antioxidant as well as having neuroprotective and anti-inflammatory uses.

For oral administration, the compositions can take the form of tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration, the compositions can take the form of tablets or lozenges formulated in conventional manner.

A preferred composition includes CBD, the preferred embodiment comprising a minimum of about 2%, more preferably about 5 to 6%, and most preferably about 7 to 10% with a preferred maximum of about 20% of the blend; turmeric, the preferred embodiment comprising a minimum of about 12%, more preferably about 14 to 16%, and most preferably about 18 to 20% and with a preferred maximum of about 25% of the blend; ginger, the preferred embodiment comprising a minimum of about 12%, more preferably about 17 to 19%, and most preferably about 19 to 22% and a preferred maximum of 25% of the blend (generally the standard will contain 5% gingerols; however, one of skill in the art would recognize that other levels of gingerols could be substituted); fennel seed powder, the preferred embodiment comprising a minimum of about 12%, more preferably about 14 to 15%, most preferably about 16 to 18%, and a preferred maximum of about 25% of the blend; valerian root, the preferred embodiment comprising a minimum of about 12%, more preferably about 14 to 15%, and most preferably about 16 to 20%, and a preferred maximum of about 25% of the blend (generally the valerian will contain about) 0.08% valerenic acids, though one of skill in the art would recognize that other levels of valerenic acids could be used; and cramp bark *Agnus castus*, the preferred embodiment comprising a minimum of about 12%, more preferably about 14 to 15%, the proprietary blend. Other embodiments can also include aloe vera, comfrey, calendula, dong quai, black cohosh, chamomile, evening primrose, *Hypericum perforatum*, licorice root, black currant seed oil, St. John's wort, tea extracts, lemon balm, *capsicum*, rosemary, *Areca catechu*, mung bean, borage seed oil, witch hazel, fenugreek, lavender.

Preferably, the disclosed compositions are taken 1-2 days before the menstrual cycle begins, presumably to combat prostaglandin synthesis, although the inventors do not wish to be constrained by their present understanding of the invention. During a menstrual cycle the patient takes 1 capsule on the onset of symptoms and up to 2 capsules a day for extra support 4-5 hours apart. Preferably, the capsules are vegan, gluten free, Non-GMO. Conveniently and preferably, the capsules are Double Zero in size to hold the recommended ingredient mg amount for a 1 capsule serving size. One of skill in the art would immediately envisage that other sizes and capsule numbers are also contemplated. Preferred embodiments for use in menstrual cycles include any female who currently suffers with menstrual cycle symptoms, generally the 12-55 age group. For menopausal relief the age group usage also includes individuals outside of this age group.

The disclosed compositions can be subdivided into unit doses containing appropriate quantities of the active component. The unit dosage form can be a packaged preparation, such as packeted tablets, capsules, and powders in paper or plastic containers or in vials or ampoules. The unit dosage can be a liquid based preparation or formulated to be incorporated into solid food products, chewing gum, or lozenges. Acceptable salts (counter ions) can be prepared by ion-exchange chromatography or other methods as are well known in the art. The formulations of the present application may be adapted to the route of administration. Those skilled in the art will recognize various synthetic methodologies that may be employed to prepare non-toxic pharmaceutical formulations incorporating the compounds described herein. A wide variety of non-toxic pharmaceutically acceptable solvents that may be used to prepare solvates of the compounds of the present application, such as water, ethanol, propylene glycol, mineral oil, vegetable oil and dimethyl sulfoxide (DMSO).

The compositions of the present application may be administered orally in dosage unit formulations containing conventional pharmaceutically acceptable carriers, adjuvants and vehicles. The formulations are in a form suitable for oral use, such as tablets, troches, lozenges, aqueous or oily suspensions, dispersible powders or granules, emulsion, hard or soft capsules, soft gel capsules, or syrups or elixirs. The formulations may be prepared according to any method known in the art for the manufacture of nutraceutical formulations and such compositions may contain one or more agents selected from the group consisting of sweetening agents, flavoring agents, coloring agents and preserving agents to provide palatable preparations. Tablets may contain the ingredients with non-toxic pharmaceutically acceptable excipients that are suitable for the manufacture of tablets. These excipients may be inert diluents, such as calcium carbonate, sodium carbonate, lactose, calcium phosphate or sodium phosphate; granulating and disintegrating agents, such as corn starch, or alginic acid; binding agents, such as starch, gelatin or acacia; and lubricating agents, such as magnesium stearate, stearic acid or talc. The tablets may be uncoated or they may be coated by known techniques to delay disintegration and absorption in the gastrointestinal tract and thereby provide a sustained action over a longer period. See, for example, the processes describing microencapsulation for controlled release found in U.S. Pat. Nos. 5,846,566 and 6,022,562, which are incorporated by reference in their entirety. Other time delay material such as glyceryl monostearate or glyceryl distearate may be employed. Formulations for oral use may also be hard gelatin capsules wherein the active ingredient is mixed with an inert solid diluent, such as calcium carbonate, calcium phosphate or kaolin, or as soft gelatin capsules wherein the active ingredient is mixed with water or an oil medium, such as peanut oil, liquid paraffin or olive oil. Aqueous suspensions contain the active materials in admixture with excipients for the manufacture of aqueous suspensions. Such excipients are suspending agents, such as sodium carboxymethylcellulose, methylcellulose, hydroxypropylmethyl cellulose, sodium alginate, polyvinylpyrrolidone, gum tragacanth and gum acacia; and dispersing or wetting agents, which may be a naturally-occurring phosphatide, such as lecithin, or condensation products of an alkylene oxide with fatty acids, such as polyoxyethylene stearate, or condensation products of ethylene oxide with long chain aliphatic alcohols, such as heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, such as polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example *arachis* oil, olive oil, sesame oil or coconut oil, or in a mineral oil such as liquid paraffin. The oily suspensions may contain a thickening agent, such as beeswax, hard paraffin or cetyl alcohol. Sweetening agents and flavoring agents may be added to provide palatable oral preparations. These compositions may be preserved by the addition of an anti-oxidant such as ascorbic acid. Dispersible powders and granules suitable for preparation of an aqueous suspension by the addition of water provide the active ingredient in admixture with a dispersing or wetting agent, suspending agent and one or more preservatives. Additional excipients, for example sweetening, flavoring and coloring agents, may also be present.

In one embodiment, the formulations may also be in the form of oil-in-water emulsions and water-in-oil emulsions. The oily phase may be a vegetable oil, such as those described herein. Of particular interest are olive oil or *arachis* oil, or a mineral oil, such as liquid paraffin or mixtures of these. Suitable emulsifying agents may be naturally-occurring gums, such as gum acacia or gum tragacanth; naturally-occurring phosphatides, such as soy bean, lecithin, and esters or partial esters derived from fatty acids and hexitol; anhydrides, such as sorbitan monooleate; and condensation products of the partial esters with ethylene oxide, such as polyoxyethylene sorbitan monooleate. The emulsions may also contain sweetening and flavoring agents. Syrups and elixirs may be formulated with sweetening agents, for example glycerol, propylene glycol, sorbitol or sucrose. The formulations may also contain a demulcent, a preservative and flavoring and coloring agents. This suspension may be formulated according to the known art using those suitable dispersing or wetting agents and suspending agents.

For administration to non-human animals, the formulations of the present application may be added to the animal's feed, food, treat, or drinking water. It may be formulated for animal feed, food, treat, and drinking water products so that the animal takes in an appropriate quantity of the compound in its diet or added as a spray to control such conditions as hot spot. The compound may be a composition as a premix for addition to the feed, food, treat, or drinking water. The composition can also be added as a food or drink supplement for humans. Dosage levels (with respect to cannabinoid mixture(s) or composition) of the order of from about 1 mg to about 250 mg per kilogram of body weight per day are useful. For example, a dosage level from about 25 mg to about 150 mg per kilogram of body weight per day, are useful. The amount of active ingredient that may be combined with the carrier materials to produce a single dosage form will vary depending upon the condition being treated and the particular mode of administration. Dosage unit forms will generally contain between from about 1 mg to about 500 mg of the cannabinoid mixture(s). For example, dosage unit forms of about 1 mg to 250 mg, 1 mg to 100 mg or 1 mg to about 80, 60, 40, 20 or 10 mg are useful. Frequency of dosage may also vary depending on the compound used. The specific dose level for any particular animal will depend upon a variety of factors including the activity of the specific compound employed, the age, body weight, general health, sex, diet, and time of administration. Also provided are packaged formulations and instructions for use of the tablet, capsule, soft gel capsule, elixir, etc. Typically, the dosage requirement is between about 1 to 4 dosages a day.

In one embodiment, the composition further comprises an additive such as a sugar or sugar derivative, such as sucrose, glucose, lactose, levulose, fructose, maltose, ribose, dextrose, isomalt, sorbitol, mannitol, xylitol, lactitol, maltitol, pentatol, arabinose, pentose, xylose and galactose, and combinations thereof. The compositions of the present application may comprise from about 0.01 to 10% by weight, 10% to 25% by weight, or about 25% to 50% by weight of the above additive, relative to the weight of the formulation.

The compositions and methods of the present application are illustrated by the examples described herein. These examples are offered to illustrate, but not to limit the claimed present application.

Using the compositions of the present application may be used effectively to alleviate a variety of symptoms selected from the group consisting of, but are not limited to dysmenorrhea (menstrual cramping), irritability, water retention, moodiness, depression, cramping, anxiety, skin changes, headaches, breast tenderness or pain, tension, weight gain, cravings, fatigue, increased stress, and hot flashes and mood swings.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

We claim:

1. A capsule consisting essentially of synergistically effective amounts of cannabidiol, turmeric, ginger, fennel, valerian root and cramp bark to alleviate pre menstrual and menstrual symptoms in a human.

* * * * *